(12) United States Patent
Hedges et al.

(10) Patent No.: US 7,242,001 B1
(45) Date of Patent: Jul. 10, 2007

(54) DEVICE FOR MEASURING WATER QUALITY

(75) Inventors: Nigel Keith Hedges, Dorset (GB); John William Proctor, Yorkshire (GB); Brian Dominic MacCraith, Dublin (IE); Hugh Joseph Masterson, Broomfield, CO (US)

(73) Assignee: Censar Technologies, Inc, Jacksonville, FL (US)

( * ) Notice: Subject to any disclaimer, the term of this patent is extended or adjusted under 35 U.S.C. 154(b) by 507 days.

(21) Appl. No.: 10/110,968

(22) PCT Filed: Oct. 18, 2000

(86) PCT No.: PCT/GB00/03996

§ 371 (c)(1),
(2), (4) Date: Oct. 1, 2002

(87) PCT Pub. No.: WO01/29541

PCT Pub. Date: Apr. 26, 2001

(30) Foreign Application Priority Data

Oct. 18, 1999 (GB) .................................. 9924537.5
Sep. 29, 2000 (GB) .................................. 0023862.6

(51) Int. Cl.
*G01N 21/17* (2006.01)

(52) U.S. Cl. ..................... 250/343; 356/339

(58) Field of Classification Search ................ 250/343; 356/339

See application file for complete search history.

(56) References Cited

U.S. PATENT DOCUMENTS

| | | | | |
|---|---|---|---|---|
| 4,555,178 A | * | 11/1985 | Harjunmaa | .................. 356/339 |
| 5,402,241 A | | 3/1995 | Jeannotte et al. | |
| 5,751,424 A | | 5/1998 | Bostater, Jr. | |
| 5,828,458 A | | 10/1998 | Taylor et al. | |
| 5,864,140 A | | 1/1999 | Owens | |
| 5,872,361 A | * | 2/1999 | Paoli et al. | .............. 250/341.8 |

FOREIGN PATENT DOCUMENTS

| | | |
|---|---|---|
| EP | 0459846 | 12/1991 |
| GB | 2234061 | 1/1991 |
| GB | 2251682 | 7/1992 |

* cited by examiner

*Primary Examiner*—David Porta
*Assistant Examiner*—Shun Lee
(74) *Attorney, Agent, or Firm*—Douglas Gene Glantz

(57) ABSTRACT

The present invention relates to a device for measuring both the color and turbidity of a liquid sample. LEDs are used as light sources and reference detectors are included to control the output of the LEDs. The device is also capable of monitoring and correcting for fouling of optical surfaces. The device is intended to be installed in-line in a mains water supply line. The device can be used in domestic water meters or on sewage treatment sites to monitor the effluent discharged back to the river.

16 Claims, 3 Drawing Sheets

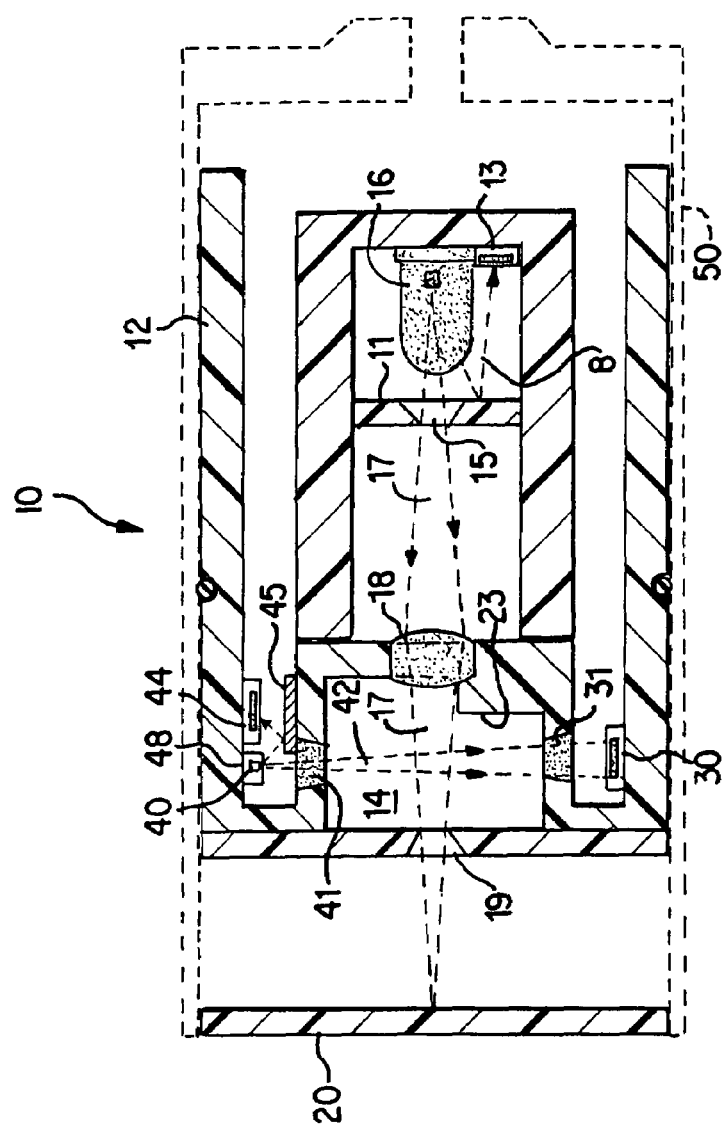
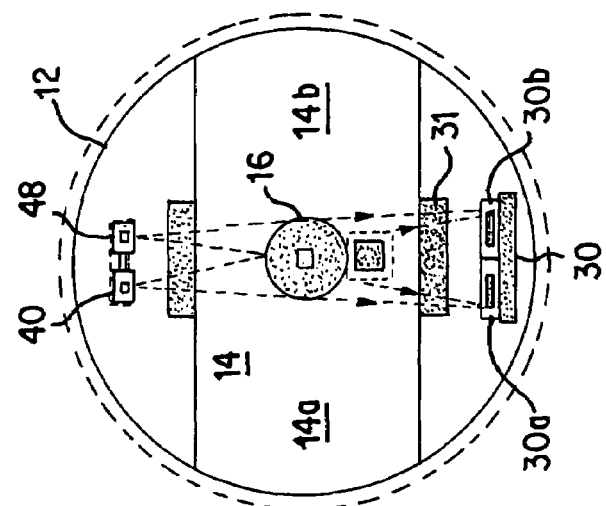

DEVICE FOR MEASURING WATER QUALITY

The present invention relates to a device for measuring water quality. More specifically, the present invention relates to a device for measuring colour and turbidity in a liquid sample.

The measurement of colour and turbidity in a liquid sample is well known. Both laboratory based and hand held devices exist. However, to date no device exists which can measure both the colour and turbidity of a liquid sample. Furthermore, no such device exists which can be used in-line in a water supply network.

Turbidity is the measurement of the particles suspended in a liquid sample. It is known to measure turbidity using the Nephelometer arrangement which measures light scattered off suspended particles at 90° with respect to a source beam. The light source typically operates in the near infrared wavelength region in order to reduce the effects that the presence of colour in the sample may have on the measurement.

However, a technical problem exists when trying to measure turbidity in a confined sample space. Randomly scattered light off the walls of the sample area can reach the detector and cause erroneous readings. This can result in a false measurement of the turbidity of the sample. This problem has been overcome in present devices by increasing the size of the sample area. However, this is not possible for an in-line device which must be able to work in a variety of sample area sizes. For example, a user may want to insert the device into a variety of water supply pipes, each of which may have a different diameter.

Colour is currently measured in liquid samples by measuring the absorbance of a beam of light transmitted through the sample. Typically, the colour of water is measured in the visible wavelength region corresponding to the colour blue.

It is an object of the present invention to provide a low cost, disposable device for use in-line in a liquid supply line which can measure both the colour and turbidity of a liquid sample.

According to the present invention there is provided a device for measuring colour and turbidity of a liquid sample, said device comprising:

a housing having a flow through sample area at one end thereof through which said liquid sample flows;

an infrared light source mounted to said housing in such a manner as to transmit a beam of infrared light through said sample area;

a main detector mounted to said housing and arranged to measure light scattered off particles suspended in said liquid sample flowing through said sample area thereby providing a measurement of turbidity of said liquid sample; and a visible light source mounted to said housing in such a manner as to transmit a beam of light through said sample area, said main detector being further arranged to measure light transmitted from said visible light source through said liquid sample flowing through said sample area thereby providing a measure of colour of said liquid sample.

According to an aspect of the present invention said device further comprises an end cap disposed on said housing distally from said infrared light source and in a manner which defines a maximum distance in which said beam of infrared light can travel. In combination with an arrangement of a lens and an aperture plate, this end cap limits unwanted scatter from the infrared light source.

According to a further aspect of the present invention said device further comprises an infrared reference detector disposed on said housing proximate said infrared light source and arranged to detect a portion of said beam of infrared light thereby facilitating control of said infrared light source.

According to yet a further aspect said device further comprises a visible reference detector disposed on said housing proximate said visible light source and arranged to detect a portion of said beam of visible light thereby facilitating control of said visible light source.

According to yet a further aspect, said device further comprises a reference light source disposed on said housing proximate said visible light source and arranged to transmit a reference beam of light in a wavelength other than that transmitted by said visible light source through said sample area in such a manner that said reference beam of light is detected by said main detector thereby enabling a measurement of biofouling. Said reference beam may also be used to improve the accuracy of turbidity measurement.

Control of the reference light source may be achieved by using a proximate detector similar to that used for the visible light source.

Preferably said infrared, visible, and reference light sources are light emitting diodes (LEDs). Preferably said infrared, visible and reference light sources have windows or other optically transparent surfaces disposed in front of them. The windows may include a conductive film arranged to facilitate prevention of a biofilm forming on the window's surface.

Preferably, the entire device is encapsulated to provide protection from high pressures found in water distribution systems.

Advantageously the device can be used in main water supply lines for distribution of potable water. The device can also be used in domestic water meters. Alternatively the device may be used on sewage treatment sites to monitor the effluent discharged back to the river.

While the principle advantages and features of the invention have been described above, a greater understanding and appreciation of the invention may be obtained by referring to the drawings and detailed description of the preferred embodiment, presented by way of example only, in which:

FIG. 1 is a cross section of a device in accordance with the present invention;

FIG. 2 is a plan view of the device from the sample area end showing the main optical components;

Figure 3:
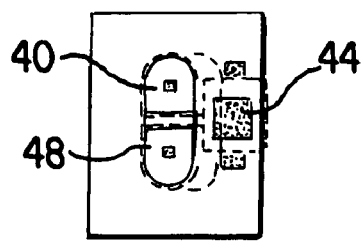
FIG. 3 is a plan view of the visible light source, the reference source, and the visible reference detector.
Figure 4:
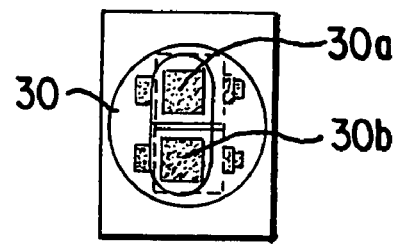
FIG. 4 is a plan view of the main detector.
Figure 5:
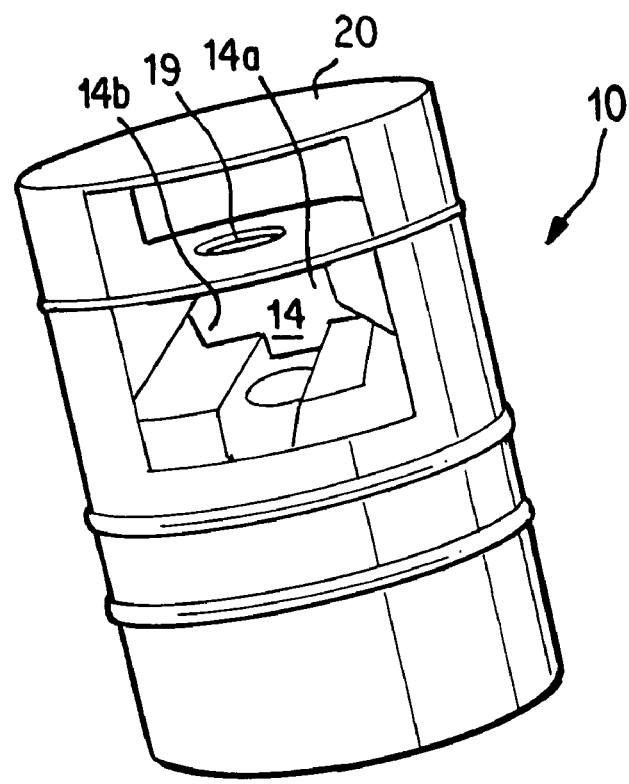
FIG. 5 is a side elevation of the device.

In FIGS. 1–5, the device 10 is shown comprising a housing 12. The housing is preferably an elongated tube-like structure made of plastic or other material suitable for immersion in potable water. Located at one end of the housing is a flow-through sample area 14. The sample area is arranged such that when the device is placed in a channel of flowing water, such as a pipe, water can flow freely through the sample area in a direction perpendicular to the plane of FIG. 1.

An infrared (IR) light source 16 is disposed within the housing. The IR light source is preferably an LED and emits light at approximately 880 nm.

An IR reference detector 13 is located next to the IR LED 16. The surface of the baffle plate 11 is sufficiently reflective in the IR wavelength region to allow a small percentage of light 8 from the IR LED to be reflected back to the IR reference detector 13. The IR reference detector is connected to the IR LED via external control connections and functions to monitor and control the output of the IR LED. As is well known an LED's output can vary with temperature change. The object of the IR reference detector and control electronics is to maintain a constant output from the IR LED, thereby improving the accuracy of the turbidity measurement.

The IR light beam passes through an aperture 15 located in the baffle plate 11 and is incident upon a lens 18 which focuses the light through a second aperture 19 and onto an end cap 20. The end cap functions to limit the travel of the IR light beam. The end cap is preferably made of plastic. Alternatively the end cap may be made of metal. The focusing lens is preferably a sphere.

A main detector 30 is disposed on the housing in the sample area approximately 90 degrees from the optical path of the IR light beam 17. The main detector has a window 31 disposed in front of it. The sides of the window 31 are cut at an angle and mounted in the housing in such a way so as to reduce the chances of light from the lens 18 directly striking the main detector. The housing 12 has a raised edge 23 in the sampled area. The raised edge functions to help prevent light from the lens 18 directly striking the main detector.

The light beam 17 enters the sample areas and is transmitted through the aperture 19 and onto the end cap 20 where it is reflected. The aperture 19 has a diameter of approximately 2 mm. The aperture 19 functions to reduce the chance of any light scattered off the end cap from re-entering the sample area where it may eventually reach the main detector 30 and cause erroneous readings.

The narrow output cone 17 of the beam of IR light along with the focusing lens 18 helps to reduce any unwanted light from directly or indirectly reaching the main detector. The main detector may be a point detector or an array of detectors. In this preferred embodiment an arrangement of two point detectors 30a, 30b is used.

The turbidity of a liquid sample is measured as follows. Liquid enters the device via openings 14a and 14b in the housing, which are located at the sides of the sample area 14. Light from the IR LED 16 is scattered of particles suspended in the liquid flowing through the sampled area. Light scattered at 90° with respect to the IR beam 17 will be detected by the main detector 30.

Prior to initial use the device must be calibrated with a clean sample, such as distilled water. Measurements are taken with the distilled water in the sample area. These measurements are an indication of stray light levels due to scattering of the housing or the end cap. The device has been designed to reduce this unwanted scattering to a minimum. The device is then set to zero and is now ready for use. When a turbid sample is introduced into the sample area any light now reaching the main detector will be an indication of the turbidity of the sample.

The use of an end cap 20 is critical in order for the device to work in a variety of pipes with varying diameters. The end cap serves to keep the amount of stray light reaching the main detector constant, thus enabling it to be eliminated via the calibration procedure previously described.

The device can be further configured to measure the colour of the liquid sample. A visible LED 40 is disposed along the side of the device such that a divergent beam of light 42 is transmitted through the sample area 14. Preferably the visible LED transmits in the blue wavelength region of the spectrum corresponding to approximately 400–460 nm. A window 41 is situated in front of the visible LED. The window is arranged in a similar manner to the main detector window 31. The main detector 30 further functions to detect the output of the visible LED. The difference in the amount of light which reaches the main detector during the calibration step and during sample measurement is an indication of the absorption of the light in the blue wavelength region.

The combined measurement of colour and turbidity gives the user of the device an indication of the clarity and quality of a water sample.

A visible reference detector 44 may be situated proximate to the visible LED 40. A reflector 45 is located opposite the visible LED 40 and visible reference detector 44. The reflector is preferably metal. A small percentage of light from the visible LED is reflected off the reflector and into the visible reference detector. The visible reference detector is connected to the visible LED via external control electronics and functions to monitor the output of the visible LED. In a fashion similar to the infrared reference detector, the visible reference detector and control electronics function to keep the output of the visible LED constant.

The device may be further configured with a second LED 48 proximate the visible LED 40. The second LED 48 is preferably of a wavelength which is not scattered by suspended particles in the liquid sample or absorbed in the blue visible spectrum region. This second LED functions as a reference LED and transmits a beam of light directly through the sample area. A small percentage of light from the reference LED is scattered off the reflector 45 and into the visible reference detector 44. The output of the reference LED is also controlled in a similar manner as the visible LED and IR LED. The main detector 30 detects the light emitted from the reference LED. A zero level is set for the reference LED during the calibration stage. Advantageously, the amount of light detected from the reference LED may be used as an indication of window fouling. This value can be used to increase the accuracy of the turbidity and colour measurements.

In order to reduce or prevent fouling of the windows, the windows 31, 41 may be coated with a conductive film. A voltage can then be applied to the coatings which can then function as a proton generator. This is a known technique for reducing window fouling. The entire device 10 can be inserted into a metal sleeve 50 which an function as a return path for the current.

As will be appreciated the LEDs and detectors can be time multiplexed at approximately one hertz. This enables the measurements to be conducted in sequence. For example, the reference LED 48 is switched on and detected by the visible reference detector 44, the output of the reference LED is then adjusted accordingly, the main detector 30 then measures the output of the reference LED and determines the amount of window fouling, next the reference LED is switched off and the IR LED 16 is switched on. The IR reference detector 13 detects and controls the output of the IR LED. The main detector 30 is then switched on and measures the turbidity of the sample. Next, the IR LED is switched off and the visible LED 40 is switched on and its output monitored and controlled by the visible reference detector 44. The main detector 30 is then switched on and measures the amount of light emitted from the visible LED thereby giving an indication of the colour of the sample. As will be appreciated the sequence of events given above can be varied without departing from the scope of the present invention.

Furthermore, the LED's may be pulsed at approximately 500 hertz and the detectors synchronised with the pulses of the LED. Advantageously, this eliminates erroneous detection of most forms of ambient light. Furthermore, this enables the device to be used in shallow locations where ambient light may reach the detectors. The overall effect achieved by the synchronous detection scheme as described above is to improve the signal to noise ratio of the measurements.

The LEDs 16, 40, 48, and detectors 13, 30, 44 are preferably surface mount components. In order to facilitate assembly of the device, the visible LED 40, reference LED 48, IR LED 16, visible reference detector 44, IR reference detector 13, and main detector 30 are disposed on the same printed circuit board. During assembly this printed circuit board is easily inserted into housing. The printed circuit board assembly is then encapsulated with an optically transparent material. Advantageously, encapsulation helps to increase the durability of the device and improves resistance to water pressure effects.

The present invention provides for a disposable device for use in-line with a water pipe for the continuous monitoring of the colour and turbidity of a liquid sample. The liquid sample may be a potable water flowing through mains water distribution networks. This may be particularly useful during refurbishment of old worn out mains water lines during which the colour and turbidity of the water is often affected.

Figure 6:
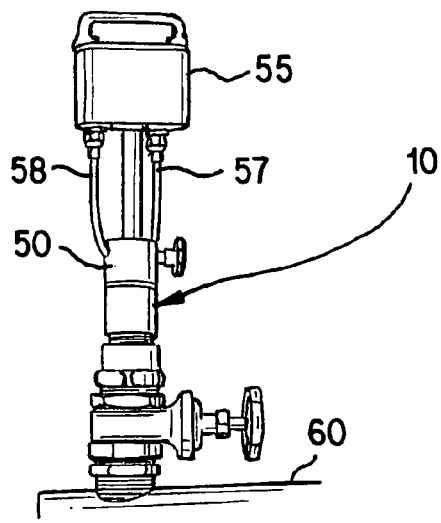
FIG. 6 shows the device inserted directly in-line with a water pipe.
Figure 7:
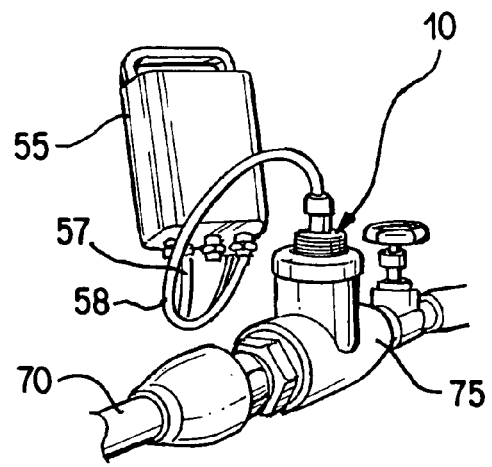
FIG. 7 shows the device inserted directly in-line with a bypass line which connects to the main water supply line.
Figure 8:
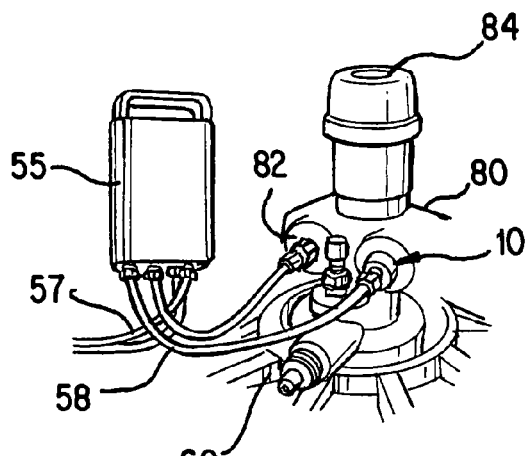
FIG. 8 shows the device along with another sensor inserted into a manifold block mounted directly in-line with a water pipe.

FIGS. 6–8 show the device 10 in operation. In FIG. 6 the device 10 is shown installed directly into a water pipe 60. The device is enclosed in a sleeve 50 which is attached to the pipe. Various electric and communications means 55 are attached to the device via cables 57 and 58. FIG. 7 shows the device 10 installed in a flowcell 75 situated on a bypass line 70. FIG. 8 shows the device 10 installed in a manifold block 80. Two further sensing device 82, 84 are also installed in the manifold block. The manifold block is attached to the water pipe 60.

Alternatively the device can be used in a wastewater treatment site to monitor the effluent discharge back into the river. Alternatively the device can be used in a district heating system where the potential for bacteria build up in the water pipes can reduce the efficiency of the heating system. The device enables for the monitoring of water quality in totally enclosed pipes, as well as open channels such as effluent from wastewater treatment sites.

The preferred wavelength of the IR LED is matched to the scattering properties of the suspended particles, which is a function of particle size. To monitor high levels of turbidity the device uses an IR LED emitting at approximately 880 nm. To monitor low level turbidity, for example, due to scattering caused by smaller sized particles, the device can be configured with an LED that emits at 550 nm. In a further embodiment the device is configured with two LED for monitoring turbidity, one emitting at 880 nm for high level turbidity measurements and one emitting at 550 nm for low level turbidity measurements. The device would function as follows. If the colour of the sample were determined to be sufficiently low the low level, the 550 nm LED would be switched on and turbidity would be measured using this LED. However, if the colour of the sample were determined to be above a predefined level, the 880 nm LED would be switched on and turbidity would be measured with this LED.

Both the measurements of colour and turbidity are important indications of the process efficiency and quality of both treated and processed waters. The parameters are also subject to regulatory control by the relevant authorities. The present invention uses an innovative optics design and integration techniques using semiconductor sources and detectors to package these measurement techniques into one compact measurement deivce. The device measurement cell is packaged in a 36 mm diameter replaceable head which is interfaced to a dedicated microprocessor-based control and signal processing electronics unit.

As will be appreciated by those skilled in the art, various modifications may be made to the embodiment hereinbefore described without departing from the scope of the present invention. For example the device may include a temperature sensor.

The invention claimed is:

1. A device for measuring colour and turbidity of a liquid sample, said device comprising;
    a housing having a flow through sample area at one end thereof through which said liquid sample flows;
    an infrared light source mounted to said housing in such a manner as to transmit a beam of infrared light through said sample area;
    a main detector mounted to said housing and arranged to measure light scattered off particles suspended in said liquid sample flowing through said sample area, thereby providing a measurement of turbidity of said liquid sample, and
    a visible light source mounted to said housing in such a manner as to transmit a beam of light through said sample area, said main detector being further arranged to measure light transmitted from said visible light source through said liquid sample flowing through said sample area thereby providing a measure of colour of said liquid sample.

2. A device as claimed in claim 1, wherein said device further comprises an end cap disposed on said housing distally from said infrared light source and in a manner which defines a maximum distance in which said beam of infrared light can travel.

3. A device as claimed in claim 1, wherein said device further comprises an infrared reference detector disposed on said housing proximate said infrared light source and arranged to detect a portion of said beam of infrared light thereby facilitating control of said infrared light source.

4. A device as claimed in claim 1, wherein said device further comprises a visible reference detector disposed on said housing proximate said visible light source and arranged to detect a portion of said beam of visible light thereby facilitating control of said visible light source.

5. A device as claimed in claim 1, wherein said infrared and/or visible light sources are light emitting diodes.

6. A device as claimed in claim 1, wherein said device further comprises a reference light source disposed on said housing proximate said visible light source and arranged to transmit a reference beam of light in a wavelength other than that transmitted by said visible light source through said sample area in a manner that said reference beam of light is detected by said main detector thereby enabling a measurement of biofouling.

7. A device as claimed in claim 6, wherein said reference light source is a light emitting diode.

8. A device as claimed in claim 1, wherein said device further comprises a pair of optically transparent windows or other optically transparent surfaces disposed in front of said infrared light source and said visible light source respectively.

9. A device as claimed in claim 8, wherein said optically transparent windows include a conductive film arranged to facilitate prevention of a biofilm forming thereon.

10. A device as claimed in claim 1, wherein said device is encapsulated with optically transparent material.

11. A device for measuring first and second physical properties of a fluid sample, said device comprising:
   a housing having at one end thereof a sample area accommodating a fluid flow therein;
   a first light source mounted to said housing, and positioned to transmit a first light beam through said fluid flow in said sample area, along a first propagation axis;
   a second light source mounted to said housing, and positioned to transmit a second light beam through said fluid flow in said sample area, along a second propagation axis which is substantially perpendicular to said first axis;
   a main detector mounted to said housing and positioned along said first axis to receive both light transmitted from said first light source and light scattered from said second light source; and
   means for alternately energizing said first and second light sources.

12. The device according to claim 11, which:
   said housing comprises an elongate body having a longitudinal axis;
   said first propagation axis is substantially paralleled to said longitudinal axis;
   said fluid flow has a flow axis that is substantially perpendicular to said longitudinal axis; and
   said second propagation axis is substantially perpendicular to both said flow axis and said longitudinal axis.

13. The device according to claim 11, wherein said first and second physical properties are color and turbidity.

14. A method for measuring first and second physical properties of a fluid in a fluid flow, comprising:
   first generating a first light beam which propagates along a first propagation axis substantially perpendicular to a flow direction of said fluid flow;
   second generating a second light beam which propagates along a second propagation axis substantially perpendicular to said flow direction and to said first propagation axis;
   providing a single light detector position along said first propagation axis for receiving light transmitted from first light source, and for receiving light scattered from said second light beam;
   alternating said first and second generating steps.

15. A method according to claim 14, further comprising:
   providing a housing having a flow chamber for guiding said fluid flow; and inserting said flow chamber into said fluid flow.

16. A method according to claim 15, wherein:
   said generating said second light beam comprises an infrared radiator; and
   said flow chamber has means for limiting a maximum distance which said second light beam can travel.

* * * * *